(12) United States Patent
Blümich et al.

(10) Patent No.: US 7,095,230 B2
(45) Date of Patent: Aug. 22, 2006

(54) NMR PROBE FOR MATERIAL ANALYSIS

(75) Inventors: Bernhard Blümich, Bergstr.31, 52159 Roetgen (DE); Michael Bruder, Hamburg (DE); Martin Klein, Aachen (DE); Karl-Heinz Krause, Chemnitz (DE); Michael Rabkin, Hamburg (DE); Jürgen Stangenberg, Hamburg (DE); Vladimir Anferov, Kalininggrad (RU); Sophia Anferova, Kalininggrad (RU); Radu Fechete, RO-TG-Mures (RO)

(73) Assignee: Bernhard Blumich, Roetgen (DE)

( * ) Notice: Subject to any disclaimer, the term of this patent is extended or adjusted under 35 U.S.C. 154(b) by 162 days.

(21) Appl. No.: 10/955,416

(22) Filed: Sep. 30, 2004

(65) Prior Publication Data

US 2005/0040823 A1 Feb. 24, 2005

Related U.S. Application Data

(63) Continuation-in-part of application No. PCT/EP03/03823, filed on Apr. 12, 2003.

(30) Foreign Application Priority Data

Apr. 14, 2002 (DE) ............................... 102 16 587

(51) Int. Cl.
*G01V 3/00* (2006.01)

(52) U.S. Cl. ...................... 324/322; 324/318

(58) Field of Classification Search ................ 324/322, 324/318, 419, 309, 307, 300; 600/410
See application file for complete search history.

(56) References Cited

U.S. PATENT DOCUMENTS

| 4,466,287 A * | 8/1984 | Repplinger et al. ............ 73/643 |
| 6,657,433 B1 * | 12/2003 | Locatelli et al. ............ 324/318 |
| 6,833,704 B1 * | 12/2004 | Murphy et al. ............. 324/318 |
| 2002/0084783 A1 * | 7/2002 | Blumich et al. ............ 324/322 |
| 2002/0089330 A1 * | 7/2002 | Blumich et al. ............ 324/322 |

* cited by examiner

*Primary Examiner*—Brij B. Shrivastav
(74) *Attorney, Agent, or Firm*—Klaus J. Bach

(57) ABSTRACT

In a unilateral NMR probe for the analysis of a material comprising at least one magnet for generating a constant time-invariant polarization field $B_0$ in the material to be analyzed and current conductors forming a radio frequency oscillation circuit for generating a pulsed radio frequency magnetic excitation field $B_1$ which is superimposed on the polarization field $N_0$ in the material, the circuit conductors are so designed as to provide several adjacent excitation fields $B_0$ with alternatingly oppositely oriented magnetic fields, whereby the current conductors generating each one of the excitation fields have a distance from each other which causes a certain penetration depth in the material to be analyzed and echoes received therefrom provide measurement values which are characteristic for the material being analyzed.

20 Claims, 10 Drawing Sheets

NMR PROBE FOR MATERIAL ANALYSIS

This is a Continuation-In-Part Application of international application PCT/EP03/03823 filed Apr. 12, 2003, and claiming the priority of German application 102 16 387.4 filed Apr. 14, 2002.

BACKGROUND OF THE INVENTION

The invention relates to an NMR probe for the analysis of materials by nuclear magnetic resonance. The probe comprises a magnet, for example an electromagnet or a permanent magnet for generating a constant time-invariant polarization field $B_o$ in the material to be examined and a radio frequency oscillation circuit for generating a pulsed high-frequency magnetic excitation field $B_1$, which is superimposed on the polarization field $B_o$ to generate echo signals S in the material which are determined by the NMR probe as material-characteristic measurement values. The echo signals can be measured on a time basis after changes of the magnetic field by way of two or more radio frequency pulses provided by the NMR probe, the third and subsequent pulses after an echo period $t_E$. The signal to be measured is generated in the area around the probe in the magnetic field wherein the components of the two magnetic fields $B_0$ and $B_1$ are orthogonal to each other.

A mechanical NMR probe such as the probe of the NMR-MOUSE (Nuclear Magnetic Resonance—Mobile Universal Surface Explorer) is a mobile measuring apparatus by which nuclear magnetic resonance is used for the analysis of materials. With an NMR-MOUSE spatial material structures can be examined. Crystalline or glass-like materials as well as soft materials such as elastomers can be examined with respect to their molecular dynamics, and also liquids and biological materials can be analyzed, see for example G. Eidmann et al. "The NMR-MOUSE, a mobile universal surface explorer", Journal of Magnetic Resonance, 1996, p. 104/109, and P Blümler et al., "Spatially resolved magnetic resonance", Wiley-VCH-publishers, 1998, p. 195/209, or A. Guthausen et al. "NMR imaging and material research", Chemie in unserer Zeit, 1998, page 73/84. The time-constant static magnetic polarization field $B_0$ is generated with the NMR-MOUSE usually by means of one or several permanent magnets. The pulsed magnetic excitation field $B_1$ is the magnetic component of a high frequency field, which is generated by a radio frequency coil, below called RF coil, as a component of an electric oscillation circuit, wherein the RF coil serves generally at the same time as the receiver coil for the echo signals S to be measured. For the polarization of the nuclear magnetization in the permanent magnetic polarization field $B_0$ and for the generation and detection of the echo signals, spatially homogeneous magnetic fields are generally not needed. NMR-Mouse probes can therefore be small and inexpensive in comparison with the normal NMR apparatus. The form and size of the ambient volume which is utilized for nuclear magnetic resonance and from which the electromagnetic signals are detected, are defined on one hand by the orthogonal components of both magnetic fields $B_0$ and $B_1$, and, on the other hand, by the band-width of the radio frequency impulses and their time pattern. The profile of the magnetic fields can be changed by the dimensioning and the arrangement of the permanent magnets and the coil of the electrical radio frequency oscillation circuit.

DE 199 28 039 A1 discloses an NMR-MOUSE apparatus for the examination of flatware of polymer materials with embedded textiles wherein several NMR-MOUSE probes form a measuring plane for supporting the flatware (3). The flatware is scanned from the surface thereof; the penetration depth of the excitation fields depends on the dimensioning of the NMR-MOUSE probe. Herein, the spatial measuring area in the material to be examined is variable in three dimensions by displacement of the NMR-MOUSE, by varying the magnetic field by auxiliary coils and by changing the high-frequency field. In connection with the present NMR-MOUSE apparatus, it is however disadvantageous that the given inhomogeneities of the permanent magnetic polarization field $B_0$ and the excitation field $B_1$ result in a dissatisfactory yield of the measuring signals from the volume area excited by an NMR-MOUSE probe by means of the radio frequency circuit. The signal to noise ratio is insufficient for demanding requirements particularly if thin material layers have to be examined.

It is the object of the present invention to improve the signal-to-noise ratio for unilateral NMR probes, wherein the penetration depth of the measuring volume taking into consideration the respective thickness of the material to be analyzed is optimized.

SUMMARY OF THE INVENTION

In a unilateral NMR probe for the analysis of materials, which comprises at least one magnet for generating a constant polarization field $B_0$ in the material to be analyzed and current conductors forming a radio frequency oscillation circuit for generating a pulsed radio frequency magnetic excitation field $B_1$ which is superimposed on the polarization field $B_0$ in the material, the circuit conductors are so designed as to provide several adjacent excitation fields $B_1$ with alternatingly oppositely oriented magnetic fields, whereby the current conductors generating each one of the excitation fields have a distance from each other which causes a certain penetration depth in the material to be analyzed and echoes received therefrom provide measurement values which are characteristic for the material being analyzed.

In order to fulfill the NMR resonance condition not only the Lamor frequency of the nuclear magnetization and the frequency of the radio frequency excitation must correspond but, additionally, also the polarization field $B_0$ and the excitation field $B_1$ of the high frequency oscillation circuit must be normal to one another. If for the formation of the transverse components disposed orthogonally to the polarization field $B_0$ several adjacent alternating excitation fields are generated, the density of the magnetic filed lines which are excited in the material volume by the radio frequency oscillation circuit and which fulfill the condition of orthogonality is increased. Also, in the given inhomogeneous polarization field therefore the signal to noise ratio is improved so as to provide for a higher signal yield. The more excitation fields are generated the higher is the sensitivity of the probe, wherein the penetration depth of the excitation fields is determined in each case by the arrangement and the form of the current conductors. Important is a characteristic distance of those current conductors or current conductor areas which generate one of the alternating excitation fields. If the excitation fields are generated for example by flat radio frequency coils, which are arranged in a plane, the radius of a conductor loop of the radio frequency coil is important for the penetration depth of the excitation field and the distance between adjacently operated radio frequency coils is important for the sensitivity. The penetration depth decreases with decreasing radius, the sensitivity increases with decreasing distance. Accordingly, the coil radius and the number of RF coils per unit area of the RF coils arranged in the plane provide for a measure for the material volume which can be analyzed by the NMR probe. In this way, the NMR probe can be adjusted by way of the selection of the distance of the current conductors of the radio frequency oscillation circuit to the thickness of the material to be examined and at the same time it can be optimized with respect to the signal-to-noise ratio.

For an NMR probe with a U-shaped magnet, particularly with a U-shaped permanent magnet preferably a meander-shaped current conductor is disposed in the area of the space between the pole legs of the magnet for the formation of the radio frequency oscillation circuit, wherein the distance between adjacent conductor passages of the meander determines the penetration depth of the excitation fields generated by the high frequency oscillation circuit. The meander-shape of the current conductor causes adjacent current conductors to have oppositely directed current flows so that adjacent meander loops generate magnetic fields with alternating magnetic field directions. The penetration depth of the excitation fields is determined mainly by the distance of the conductors. However, with uniform meander loops, the distance between the conductors also determines the sensitivity of the probe for thin samples. The sensitivity of the NMR probe is higher the smaller the distance between the conductor passages is. A maximum sensitivity is achieved when the depth of the measuring volume is tuned to the sample thickness by an appropriate selection at the conductor passage spacing taking into consideration the orthogonality condition.

For optimizing of the signal-to-noise ratio, it is expedient to generate the excitation fields in an area $B_0$ of the polarization field wherein the orthogonality conditions are fulfilled with approximately uniform magnetic field strength. The meander-shaped current conductor is therefore preferably arranged at a distance h from the gap between the pole legs of the U-shaped magnet in whose effective area the polarization field $B_0$ has a uniform magnetic field strength.

Preferably, the current conductor or conductors of the radio frequency oscillation circuit form several conductor loops in a plane extending normal to the polarization field $B_0$, which are arranged adjacent to one another and are operated in a counter-current fashion. Accordingly, between the conductor loops, excitation fields with alternating magnetic field directions are generated. The distance characteristic for the penetration depth is the radius r of the conductor loops. The sensitivity of the NMR-MOUSE probe is again determined by the number of the conductor loops per unit area of the plane, in which they are arranged. The smaller the conductor loops and the tighter they are arranged, the higher is the sensitivity of the probe for thin layers.

The planar conductor loops which are arranged adjacent to one another can be formed by a single conductor and arranged in series or in parallel. In order to be able to recognize with an NMR probe also local differences in the material composition, there are several radio frequency coils (RF coils) arranged in the plane normal to the polarization field $B_0$ which are operated in anti-phase and are not only connected in series but can also be operated individually. During individual operation, in each case, local measurement values can be analyzed and differences in the materials can be determined between the measurement locations of the various radio-frequency coils.

Preferred conductor loop shapes are conductor loops in the form of the number 8 or clover leaf shape or a snake line shaped conductor loops.

It is expedient if the current conductors are disposed in, or on, a separate carrier structure which can be connected to the magnet which generates the polarization field $B_0$. As carrier material, an electrically non-conductive material is used, particularly silicon, glass or a ceramic material. The carrier structure may consist of a material which is particularly selected for the examinations to be performed by the NMR probe. In order to avoid wetting, the carrier surface may be hydrophobic. In order to be able to mount the carrier onto the polarization magnet in a simple manner a support is provided for the carrier by which the carrier can be fixed by magnetic forces. The support preferably consists of a steel sheet.

In order to obtain measurement results which are independent of temperature variations, the NMR probe is preferably provided with a temperature controller. As temperature control medium expediently a temperature-controlled gas stream is used. For adjusting a constant temperature preferably a Peltier element is used which is controlled by a temperature sensor.

The small measuring volumes achievable with the NMR probes at small characteristic distances of the current conductors forming the radio frequency oscillation circuit can be excited advantageously by short RF impulses of few microseconds duration. Within such a small material volume, there are also only small field variations in the polarization field $B_0$ so that for the coil arrangement according to the invention optimal orthogonality conditions between the polarization field $B_0$ and the excitation field $B_1$ are obtained. The filling factor which indicates the ratio of the material volume to be analyzed and the measuring volume which is collected by the NMR probe is therefore adjustable for thin material samples in an optimal way. For thin materials, the signal to noise ratio can be maximized with the use of miniaturized RF coils. Such NMR probes are therefore very suitable for the analysis of surface coatings of electrically non-conductive materials, for example, for the analysis of coatings or sheet covers. Another preferred application is the analysis of thin materials, particularly of foils, of membranes, paper sheets and many other thin materials for determining their thicknesses and homogeneities.

Particularly important for the invention is the use of unilateral NMR apparatus as sensors. To this end, it is expedient to cover the current conductors which generate the excitation field $B_1$ at their free surface remote from the polarization magnet for generating the polarization field $B_0$ with a layer which reacts sensorically to the surrounding area with a change of the echo signals to be measured by the NMR probe. Such an application and formation of the NMR probe is independent from an arrangement of several RF coils. As sensor layer, the current conductors may be covered by a sensor foil. However, preferably the current conductors are coated with a coating which includes molecules that are chemically functionalized for the particular application. The field of application for an NMR probe of this type is very wide; for its use only a layer needs to be applied to the NMR probe which is chemically adjusted to the expected reaction and which, with such a reaction, changes the echo signal measured by the NMR probe.

Because of the high quality and suitability for the analysis of thin layers and because of the high sensitivity for surface areas the NMR probes described above are highly suitable as sensors. The invention will be described below in greater detail on the basis of the accompanying drawings.

DETAILED DESCRIPTION OF PARTICULAR EMBODIMENTS

Figure 1:
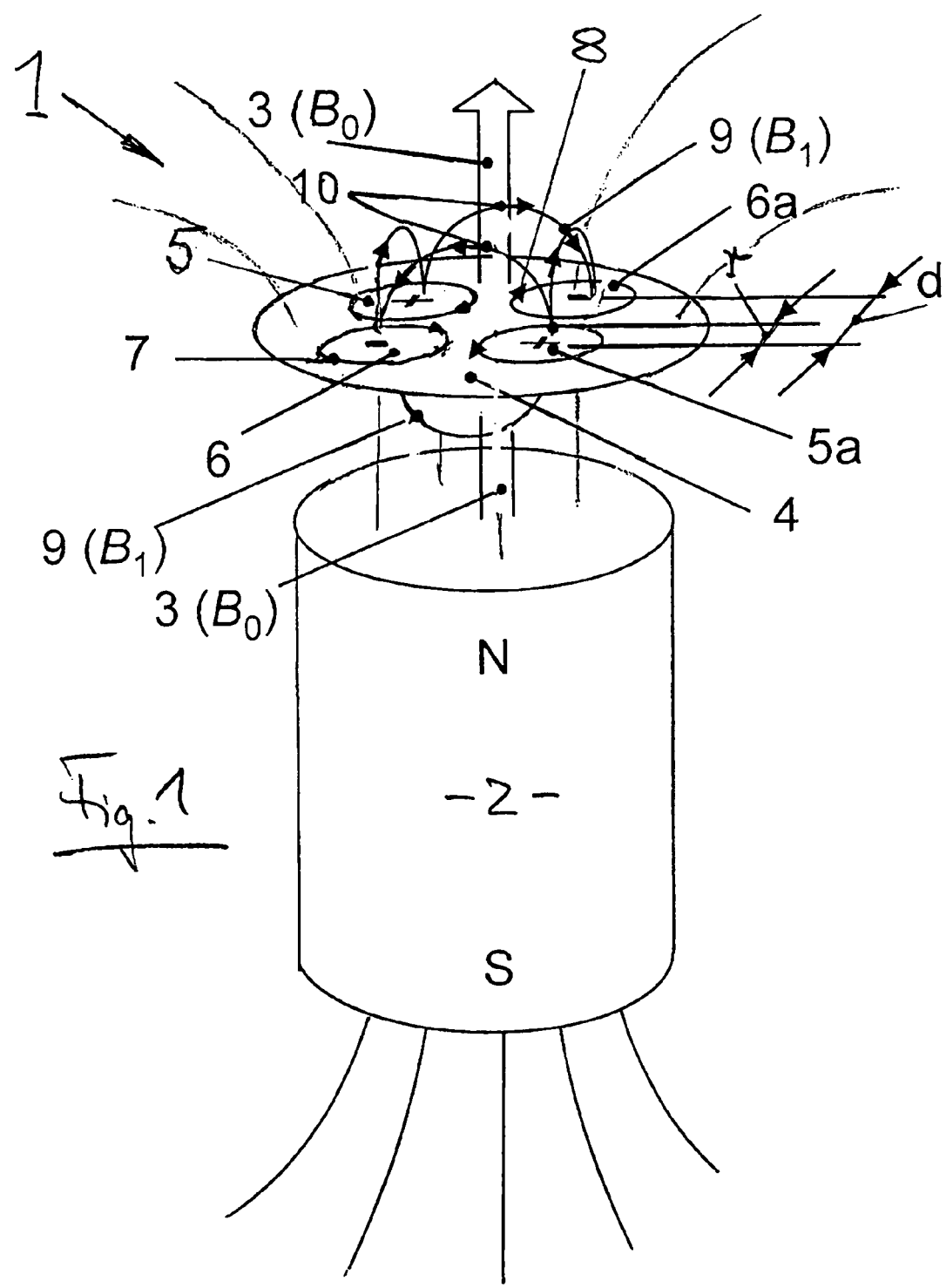
FIG. 1 serves for the explanation of the principle on which the invention is based.

In FIG. 1, the principle on which the invention is based is explained on the basis of a particular embodiment. FIG. 1 shows schematically an NMR probe 1, for example of the type NMR-MOUSE, in a static polarization field $B_0$, which is generated by a permanent magnet 2 with a magnetic north (N) and south (S) pole, and the magnetic field lines 3 thereof, with several radio frequency coils (RF-coils) 5, 5a, 6, 6a being arranged in a plane extending normal to the polarization field $B_0$. Upon use of the NMR-probe for material analysis the polarization field $B_0$ serves for the polarization of the nuclear spins in the material which is to be examined; and the RF coil for the generation of pulsed magnetic excitation field $B_1$, which is super-imposed on the highly inhomogeneous time-constant permanent magnetic polarization field $B_0$ for the excitation of nuclear spin echoes (S). The obtained nuclear spin echoes are the characteristic values for the material to be examined by the NMR probe in the form of measured signals.

Because of the inhomogeneities of the permanent magnetic polarization field $B_0$ the known NMR probes with the radio frequency magnetic excitation fields $B_1$, generated by a simple RF coil fulfill the orthogonality conditions required for a desired signal only in few volume ranges of the material to be examined, that is, where the components of the two superimposed magnetic fields $B_0$ and $B_1$ are normal to each other. In FIG. 1, in accordance with the invention, in the plane 4 which extends normal to the polarization field $B_0$ (normal to the magnetic field lines 3) several flat RF coils 5, 5a, 6, 6a, are disposed wherein all RF coils are so arranged that the current conducting conductor loops thereof extend parallel to the plane 4 and adjacent RF coils 5, 6 and 5a, 6a respectively are operated in anti-phase with respect to each other, see in FIG. 1, the current direction arrows 8 at the conductor loops 7. In FIG. 1, schematically only one conductor loop is shown for each RF coil. Of course, each RF coil may include several conductor loops arranged parallel to the plane 4, particularly spiral coil windings. Because of the operation of adjacent RF coils in an opposite phase relationship oppositely oriented magnetic fields are formed between the RF coils. In FIG. 1, the directions of the magnetic fields generated by the RF coils 5, 5a are indicated by a (+) sign and the magnetic fields generated by the RF coils 6, 6a are indicated by a (−) sign. Between the adjacent RF coils therefore alternatingly oriented excitation fields $B_1$ with magnetic lines 9 and transverse components 10 are generated which extend in the magnetic field area above the RF coil normal to the polarization field $B_0$. Of the transverse components FIG. 1 shows for simplicity reasons in each case only the transverse component of the excitation fields $B_1$ in the apex of the magnetic field lines 9, which optimally fulfill the orthogonality condition necessary for the generation of the measurement signals.

The excitation fields $B_1$ penetrate further into the material to be examined the larger the coil radii of the conductor loop 7 of the RF coils are. The penetration depth of the excitation fields increase with the coil radius r of the adjacent RF coil in the plane 4. With increasing coil radii expediently also the distance d between the RF coils increases which determined the density of the orthogonal transverse components in the penetration volume. With increasing distance d between the RF coils, the density of orthogonal magnetic transverse components in the penetration volume decreases. If a material of a certain thickness is to be examined by the NMR probe the coil radius r and the distance d of the RF coils are to be so adapted that, under consideration of the orthogonality conditions, the measuring volume corresponds to the material volume to be examined with the highest possible sensitivity.

Figure 2:
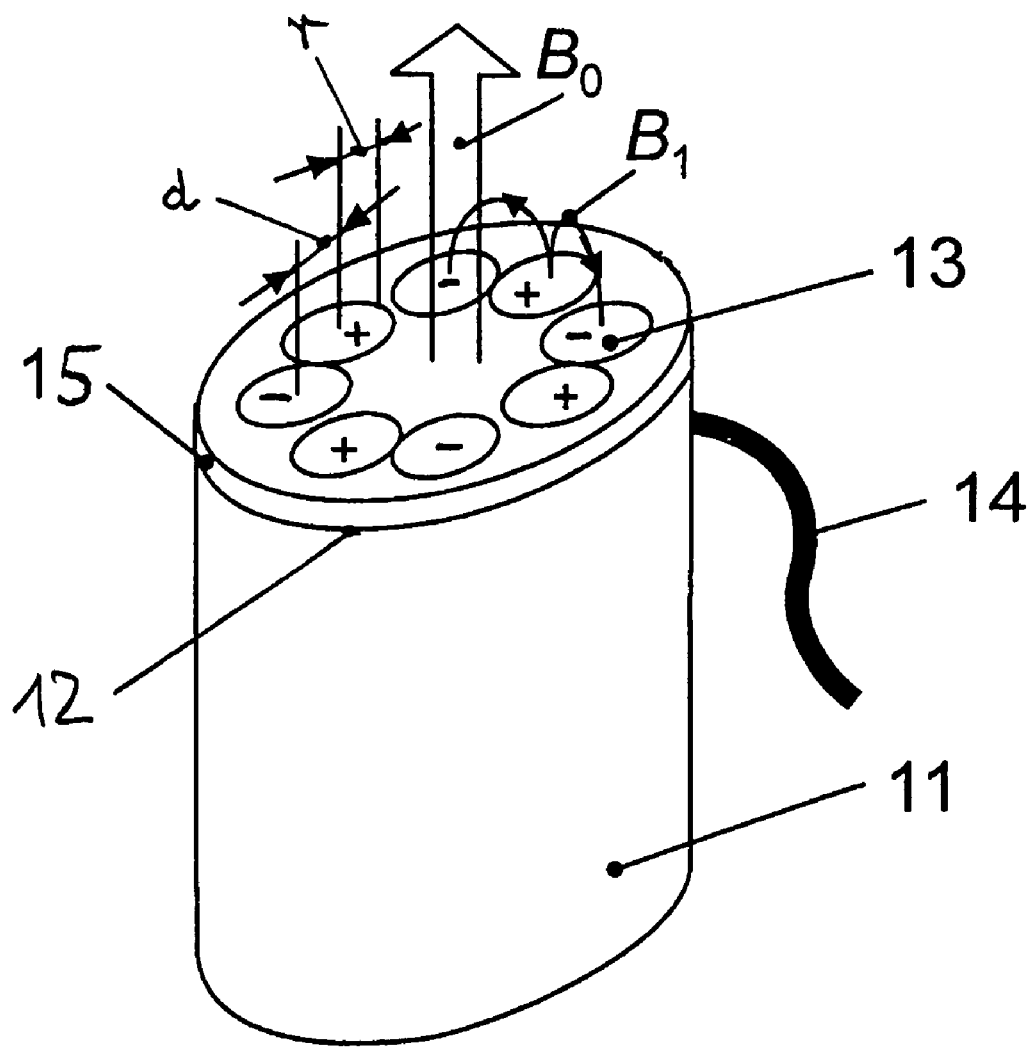
FIG. 2 shows an NMR probe with RF coils on the pole face of a rod-like permanent magnet.

FIG. 2 shows schematically an NMR probe with a rod-like permanent magnet 11 providing for a permanent magnetic polarization field $B_0$ and a pole face 12 on which in the embodiment eight octagonally adjacent RF coils 13 are arranged with flat conductor loops disposed parallel to the pole surface. Adjacent RF coils are operated in anti-phase and alternately generate oppositely oriented magnetic excitation fields $B_1$ with transverse components oriented orthogonally to the permanent magnetic polarization field $B_0$. The directions of the magnetic fields generated by the RF coils 13 are again indicated by positive (+) and respectively, negative (−) signs.

The penetration depth and sensitivity of the NMR probe depend—as indicated in the example of FIG. 1—on the coil radius r of the conductor loops and the distance d between adjacent RF coils 13. Each of the RF coils can be operated in the example of FIG. 2 individually. This has the advantage that with the NMR probe at the same time average values of the measuring values determined by the individual RF coils can be obtained, for example in a time-shaped fashion, but also material specific deviations of the same measurement values at locally different locations of the material, that is, variants of the measurement values for locally different material areas can be determined. If the RF coils are not individually operated but connected in series or in parallel—while maintaining alternatingly generated excitation fields—in one measurement an average value of the measurement values of all the RF coils can be obtained.

For the electric power supply of the RF coils and for the back transmission of the measuring signals received by the RF coils in the embodiment shown an RF supply cable 14, which is connected to the RF coils, is provided. The RF coils are embedded in, or disposed on, a carrier 15 consisting of glass or semiconductor crystal discs wherein the surface of the carrier 15 can be chemically modified. To prevent wetting with water, the carrier may be provided for example with a hydrophobic surface which, since water contains protons, is advantageous for obtaining a noise-free measuring signal.

Figure 3:
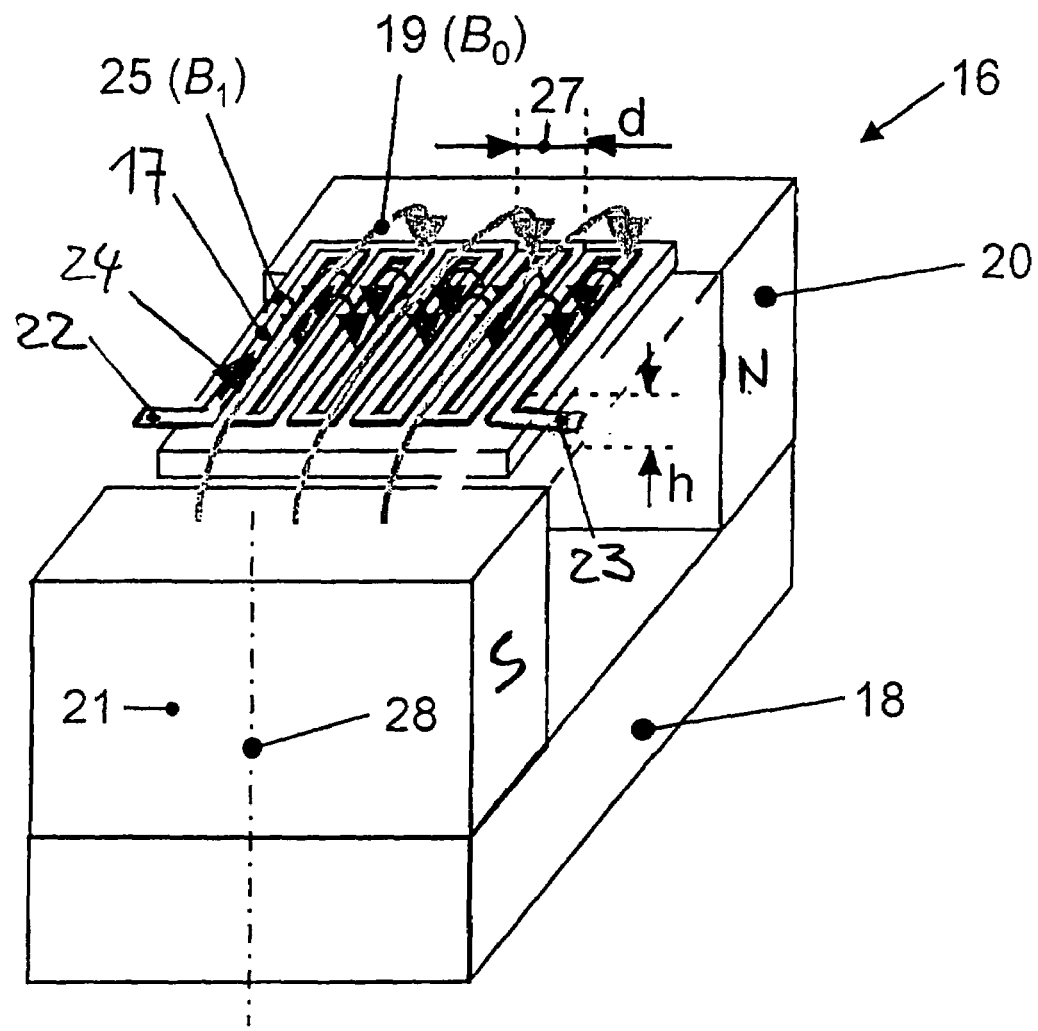
FIG. 3 shows an NMR probe with a meander-shaped RF coil.
Figure 3A:
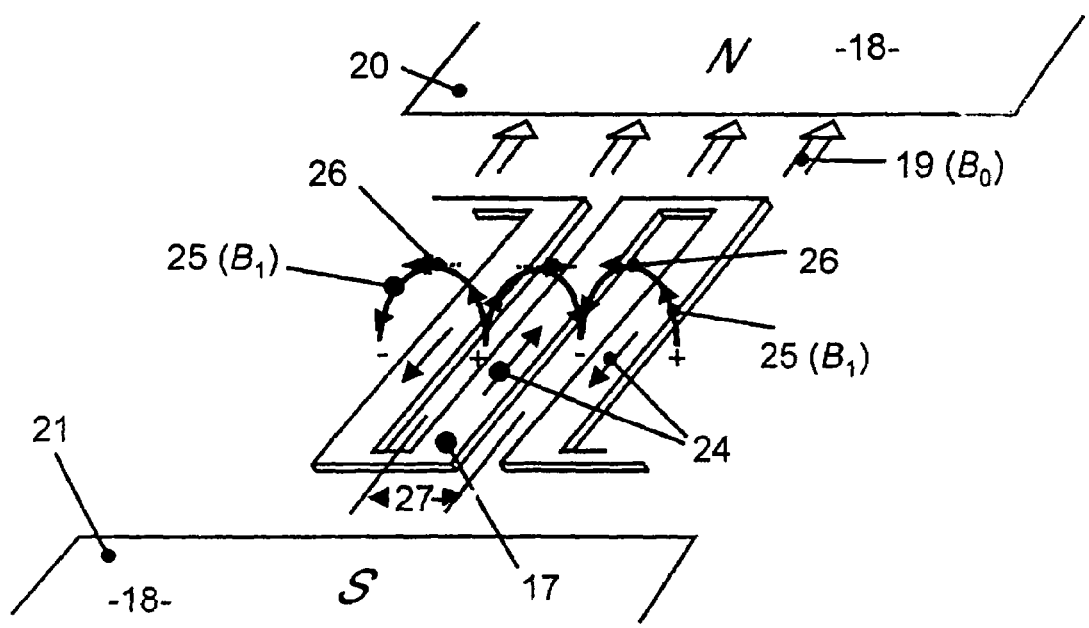
FIG. 3a shows a section of an NMR probe according to FIG. 3 in an enlarged scale.

FIG. 3 shows an NMR probe 16 with an RF coil with a meander-shaped current conductor 17. FIG. 3a shows a section of the RF coil in an enlarged representation. The current conductor 17 is disposed in a U-shaped permanent magnet 18, which generates a polarization field $B_0$ shown schematically in FIG. 3a by parallel magnetic field lines 19. The RF coil is arranged between pole legs 20, 21 of the U-shaped permanent magnet 18 and provided at its ends with current connectors 22, 23. In FIG. 3a, the current flow in the meander sections of the current conductors 17 is marked by current direction arrows 24. Adjacent meander sections have opposite current flow directions. In this way, alternatingly anti-phase magnetic excitation fields $B_1$ are formed between the meander windings of the RF coil. The directions of the magnetic fields between the meander windings are indicated in FIG. 3a again by positive (+) and negative (−) signs. The excitation fields $B_1$, the magnetic field lines of which and their orientation are schematically indicated in FIG. 3a are superimposed over the polarization field $B_0$ formed between the pole legs 20, 21 and generate in the magnetic field space above the meander shaped RF coil transverse components 26, which extend normal to the polarization field $B_0$. Of the transverse components 26, FIG. 3a again shows for clarity reasons only the transverse components of the excitation fields $B_1$ in the apex of the magnetic field lines 25.

The penetration depth of the excitation fields is determined with the meander-shaped RF coil by the distance between adjacent meander windings. The distance 27 corresponds to twice the coil radius r of a conductor loop 7 of the RF coils 13 of the embodiment as shown in FIG. 2. The distance 27 however determines also the sensitivity of the NMR probe 16 since it corresponds also to the distance d between the adjacent RF coils 13 according to FIG. 2. The sensitivity of the NMR probe according to FIG. 3 therefore decreases with increasing distance 27 between the meander windings of the current conductor 17. Therefore, a meander-shaped RF coil is optimized in penetration depth and sensitivity by determining the distance 27 between the meander windings.

Figure 4:
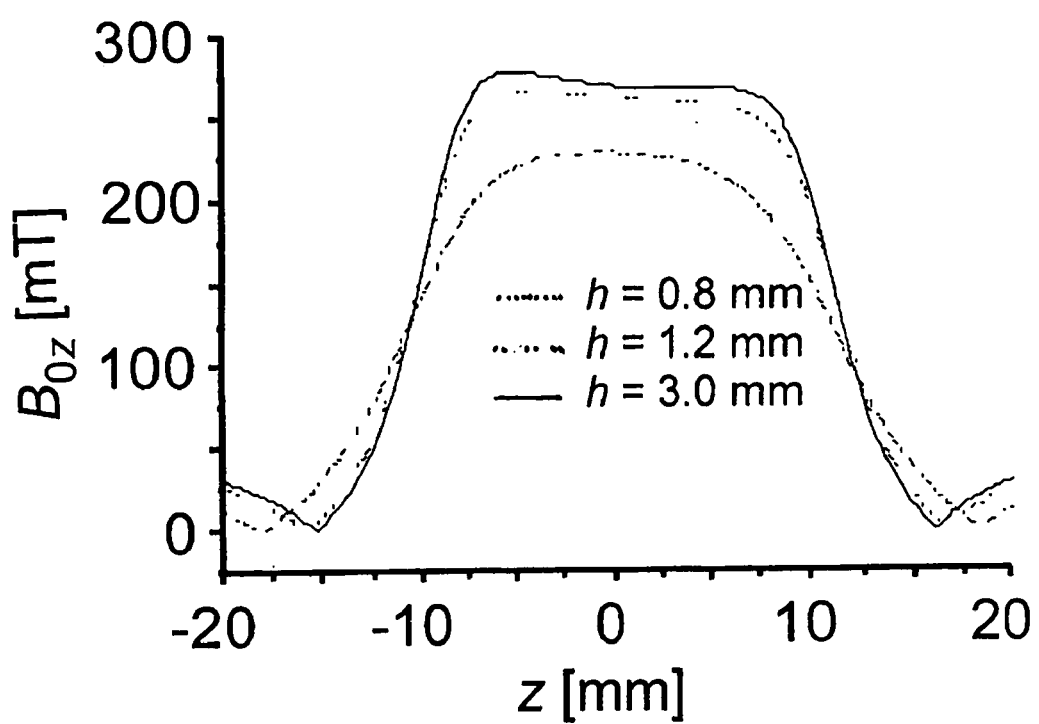
FIG. 4 shows the positioning of an NMR coil according to FIG. 3.

FIG. 4 shows the course of the polarization field $B_0$ transverse to the gap between the pole legs 20, 21 of the permanent magnet 18 for different heights h over the gap independent of the RF coil 17 according to FIG. 3 and without any effects of the RF coil on the formation of the polarization field $B_0$. FIG. 4 shows on the ordinate the permanent magnet field strengths $B_0$ in mT (T=Tesla) as measured with different distances h as parameter, and on the base the gap width 2 measured as the distance (in mm) from the line of symmetry of the permanent magnet 18. From FIG. 4, it is apparent that the permanent magnet field strength $B_0$ becomes uniform only above a certain distance h from the gap over the gap width, in the exemplary embodiment, at a gap width between the pole legs of 20 mm, only with a distance of h=1.2 mm. At a distance h of 3.0 mm a maximum is obtained. With this distance, there is an almost constant permanent magnet field strength $B_0$ of 265 mT over the whole gap width between the pole legs. In this area also the resonance condition is fulfilled at all locations at the same frequency. If the meander shaped RF coil 17 is positioned at the distance h of 3 mm from the gap, the sensitivity of the NMR probe is improved particularly for the analysis of thin material surface areas.

Figure 5:
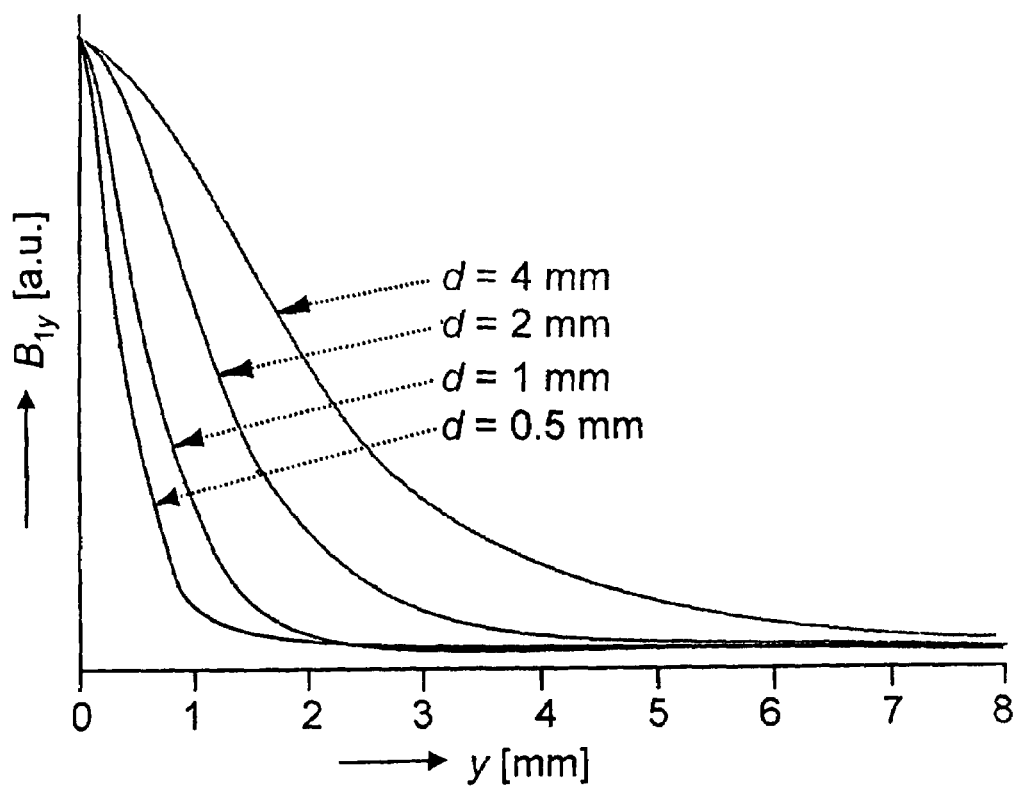
FIG. 5 shows the magnetic field formation of an RF coil according to FIG. 3.

The penetration depth of excitation fields $B_1$, which, according to FIG. 3, is achieved with an NMR probe 16 with increasing conductor distance d, is presented in FIG. 5. As RF coils 17 meander coils of a 0.5 mm wide conductor strip with different distances between the meander shaped conductor strips of ½, 1, 2 and 4 mm were used. FIG. 5 shows that, with increasing conductor strip distances, the penetration depth of the excitation field $B_1$ grows and the excitation field becomes effective at increasing distances y from the coil surface. In FIG. 5, the transverse component of the excitation field $B_1$, which extends normal to the polarization field $B_0$ is shown dimensionless (a.u.) in order make the change of the penetration depth more apparent.

Figure 6:
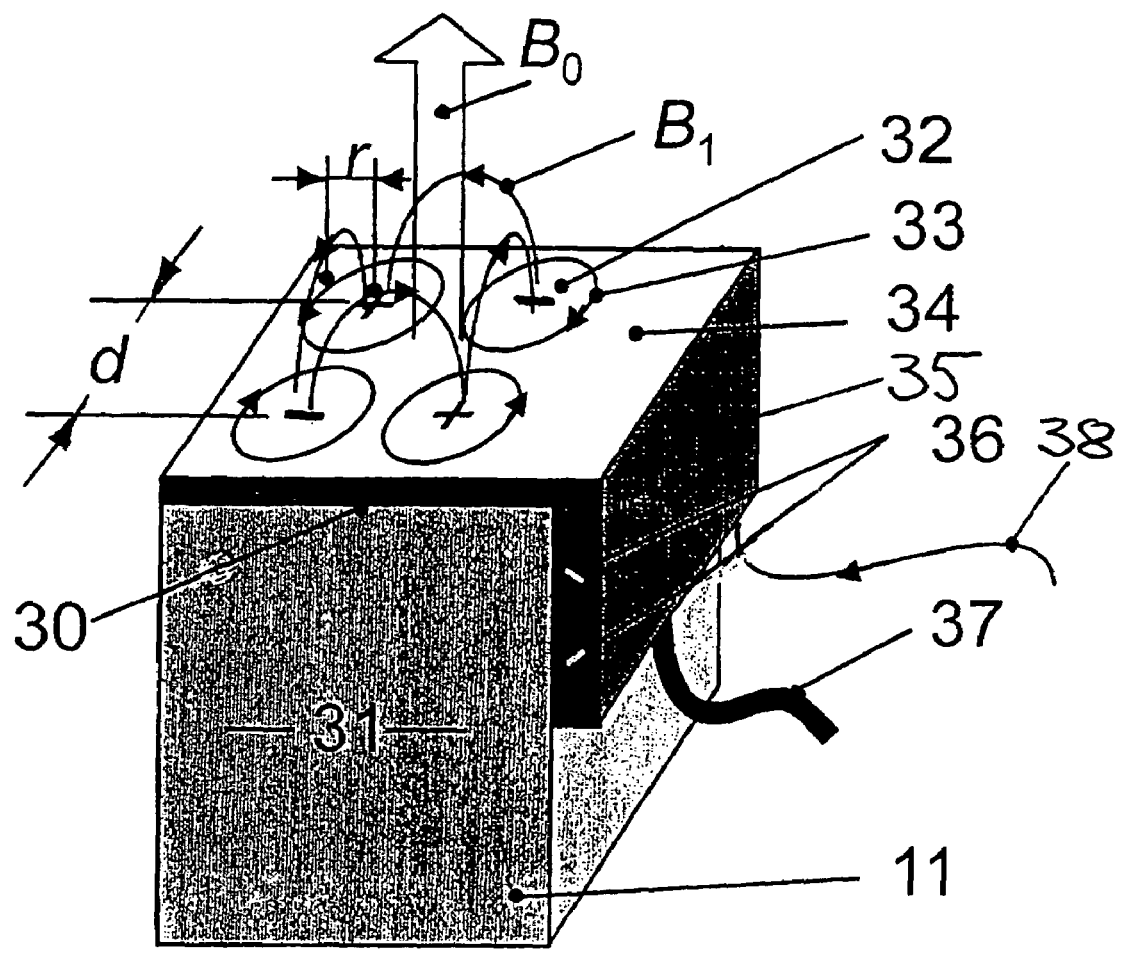
FIG. 6 shows an NMR probe with clover leaf shaped conductor loops of an RF coil.

Another embodiment of an NMR probe is shown in FIG. 6. In this embodiment four RF-coils 32 (in a so-called clover leaf form or in the form of a double "8") are arranged on one of the pole faces 30 of a rectangular rod magnet 31, only one conductor loop being schematically shown. Each RF coil may of course include several conductor loops, in particular spiral coil windings. The current directions present in the conductor loops are schematically shown in FIG. 6 by the current direction arrows 33. The magnetic fields generated in this way alternatingly opposite directions by the conductor loops are again indicated by positive (+) and negative (−) signs. Between adjacent conductor loops excitation fields $B_1$ strongly orthogonal transverse components to the polarization field $B_0$ are generated in the magnetic field area above the RF coils 32. Also in this embodiment, the penetration depth and the sensitivity of the NMR probe depend on the geometric dimensions for the coil radius r of the conductor loops and the distance d between adjacent RF coils. The smaller the coil radii of the conductor loops are, the smaller is the penetration depth and the tighter they are arranged on the pole surface, the smaller is also the distance d between them and the higher is the sensitivity of the NMR-probe for thin materials.

The RF coils 32 are embedded in a carrier 34 with a tuning box 35 being attached to one of the side surfaces of the rod magnet 31. The tuning box 35 includes tuning and matching capacitors 36 and a connection for an RF cable 37. The carrier 34 is provided with a thin steel sheet by way of which it is attached to one side of the magnet 31. In this way, an exchange of carriers with different RF coil types is easily possible. A temperature-controlled gas flow can be conducted through the carrier 34 and the power supply part 35 for controlling the temperature of the RF coils 32. The RF coils 32 are preferably operated at room temperature.

Figure 7:
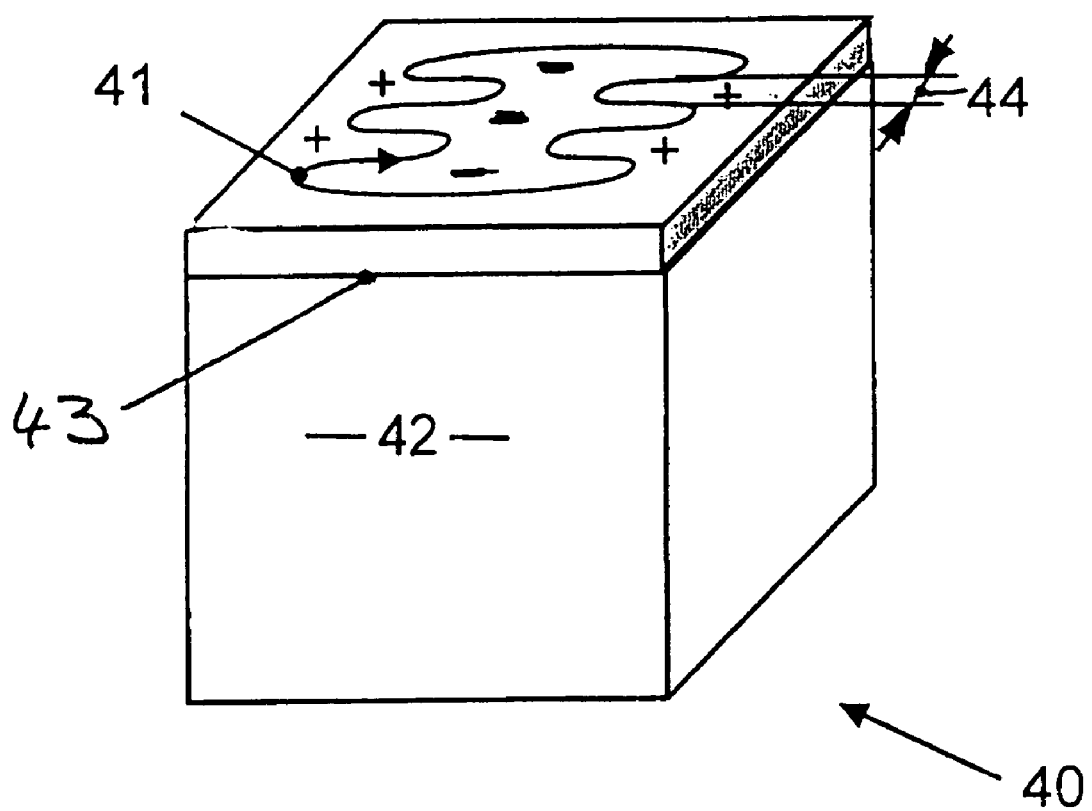
FIG. 7 shows an NMR probe with a snake line shaped RF coil.

Another embodiment of an NMR-probe is shown in FIG. 7. With this NMR probe, the RF coil has a current conductor 41 of a snake line shape and is arranged on one of the pole faces of a rod magnet 42, in the embodiment shown on the pole face 43, in such an arrangement, that adjacent alternatingly oppositely oriented excitation fields $B_1$ are generated. The magnet field directions obtained between the snake-line shaped sections of the conductor arrangement are indicated in FIG. 7 again by positive (+) and negative (−) signs. The distance characteristic for the penetration depth and the magnetic field strength corresponding to the sensitivity of the NMR probe 40 is the distance 44 between the individual windings of the conductor arrangement.

Figure 8:
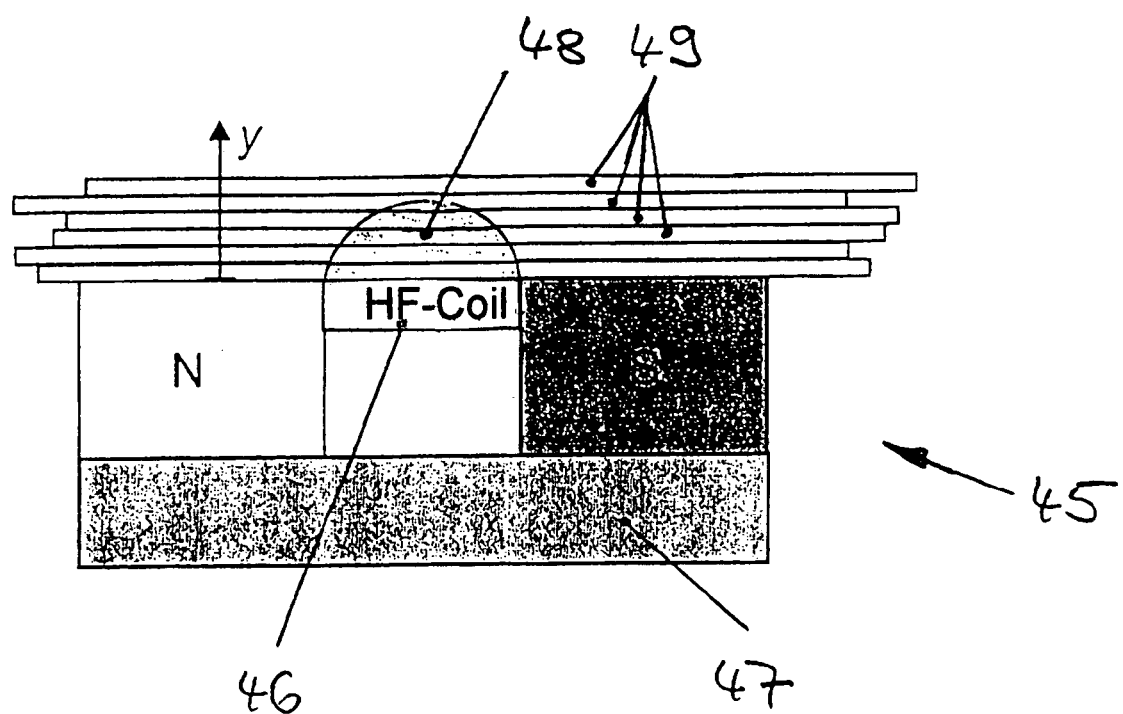
FIG. 8 shows an NMR probe for measuring the thickness of materials and FIG. 9 shows the signal amplitude depending on the material thickness.
Figure 9:
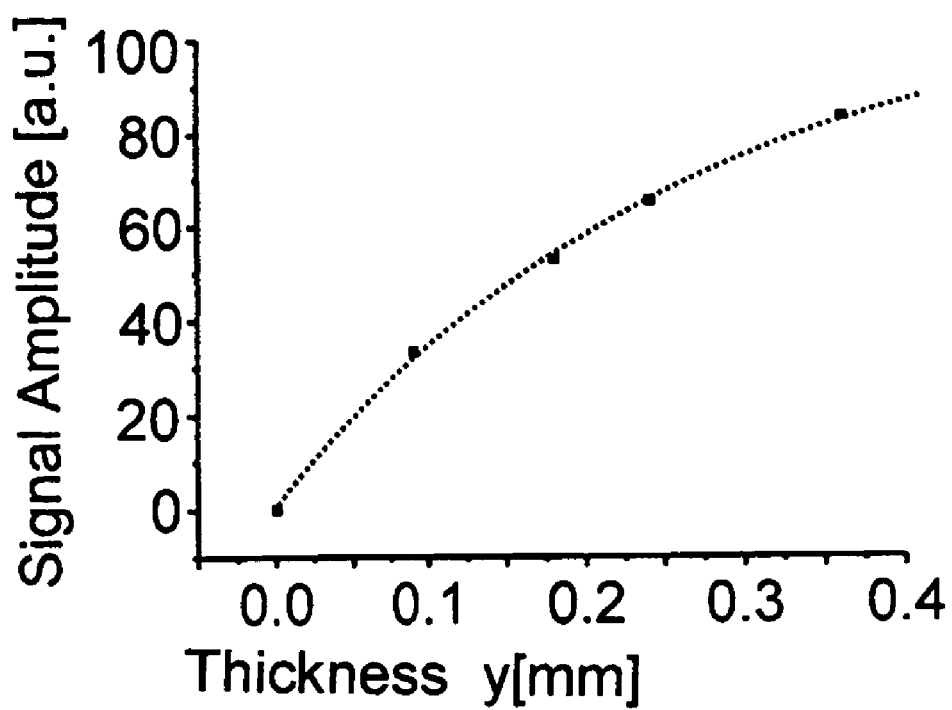

FIGS. 8 and 9 show an embodiment for measuring the thickness of a membrane. FIG. 8 shows schematically an NMR probe of the type NMR-MOUSE 45 with a meander shaped RF coil 46 arranged between the pole legs (N) and (S) of a U-shaped permanent magnet 47. An embodiment of an NMR probe of this type is shown already in FIG. 3. The NMR probe comprises as measuring range a sensitive volume 48 into which membranes 49 are placed one after another for measuring their thicknesses. FIG. 9 shows the measured result: The signal amplitude (in % of the ordinate)

measured with the probe in each case is shown depending on the membrane thickness (in mm on the abscissa). As apparent from FIG. 9, the values of the signal amplitude do not increase linearly with the membrane thickness, rather a weaker than linear dependency is obtained. This follows from the spatial distribution of the sensitive volume 43 over the NMR probe. The material volume covered by a measuring area decreases with increasing material thickness, see FIG. 8. The radius of the measuring area determines the maximum material thickness that can be measured.

For use as a sensor unilateral NMR probes are particularly suitable since they can be covered, above the RF coils which generate the excitation field, with a sensorically reacting layer. Particularly NMR probes with current conductors which are embedded in carriers—see embodiments according to FIGS. 2, 6, 7—can be provided on the outer carrier surface with a sensor layer. As sensor layers only suitable foils are needed since, particularly NMR probes of the type NMR-MOUSE with alternating excitation fields generated by a corresponding shape of the current conductors, have a high sensitivity in the areas near the surface of the structure to be measured.

What is claimed is:

1. A unilateral NMR probe for the analysis of a material, comprising at least one magnet for generating a constant polarization field $B_0$ in the material to be analyzed, current conductors forming part of a radio frequency oscillation circuit for generating a pulsed radio frequency magnetic excitation field $B_1$, which is superimposed onto the polarization field $B_0$ in the material to be analyzed, said current conductors being so designed as to provide several adjacent excitation fields with alternately oppositely oriented magnetic fields, wherein the current generating the magnetic excitation fields have a distance from each other which causes a certain penetration depth in the material to be analyzed and echoes received therefrom provide measurement values which are characteristic for the material being analyzed.

2. An NMR probe according to claim 1, wherein said at least one magnet for generating a constant polarization field ($B_0$) is a U-shaped magnet (18, 47) with spaced pole legs forming a gap area therebetween and a meander-shaped conductor (17) is arranged in the gap area between the pole legs (20, 26) of the magnet for forming the high frequency field, said conductor having adjacent conductor sections spaced from each other by a distance (d) which determines the penetration into the material to be analyzed of the excitation field generated by the high frequency oscillation circuit.

3. An NMR probe according to claim 2, wherein the meander-shaped circuit conductor (17) is arranged at a distance h from the gap between the pole legs (20, 21) of the U-shaped magnet (18) wherein the distance h is determined by an area of uniform magnet field strength of the polarization field $B_0$.

4. An NMR probe according to claim 1, wherein, in a plane normal to the polarization field (4, 13, 30, 43) for forming the radio frequency oscillation circuit, several conductor loops (13, 32, 41) are arranged adjacent to one another and operated in an anti-phase, wherein the radius (r) and the distance d of the conductor loops from one another determine the penetration depth of the field into the material to be analyzed.

5. An NMR probe according to claim 4, wherein several radio frequency coils (RF coils 13, 32, 41), which are operated in anti-phase are arranged in the plane.

6. An NMR probe according to claim 4, wherein at least one coil loop (32) in the shape of an 8 is provided so as to be operated in an anti-phase relationship.

7. An NMR probe according to claim 4, wherein at least one cloverleaf shaped conductor loop (32) is used.

8. An NMR probe according to claim 4, wherein the conductor loop (41) has a snake line like shape.

9. An NMR probe according to claim 1, wherein the current conductor (13, 32, 41) is disposed in, or on, a carrier (15).

10. An NMR probe according to claim 9, wherein said carrier (15) consists of one of a semiconductor crystal, glass, and ceramic material.

11. An NMR probe according to claim 8, wherein said carrier has a hydrophobic surface.

12. An NMR probe according to claim 9, wherein the current conductor carrier (35) is provided in the magnetic mounting means for attachment to the polarization magnet of the probe.

13. An NMR probe according to claim 12, wherein the magnetic mounting means is a steel sheet mounted to the carrier (34).

14. An NMR probe according to claim 1, wherein a temperature controller is provided for the probe.

15. An NMR probe according to claim 14, wherein a temperature controlled gas flow (38) is conducted through the probe for cooling the probe.

16. An NMR probe according to claim 1, wherein the probe is used for the analysis of surface coatings of electrically non- or weakly conducting or electrically anisotropic material.

17. An NMR probe according to claim 1, wherein the probe is used for the analysis of thin materials including foils, membranes and paper sheets.

18. An NMR probe according to claim 17, wherein the probe is used to determine the thickness of the material.

19. An NMR probe according to claim 1, wherein the probe is used as a sensor.

20. An NMR probe according to claim 19, wherein the current conductor is provided at its free surface opposite the polarization magnet with a layer which reacts to the adjacent ambient sensorically in such a way that the echo signals S generated by the excitation fields are changed in a certain way.

* * * * *